United States Patent
Lau et al.

(10) Patent No.: US 7,590,440 B2
(45) Date of Patent: Sep. 15, 2009

(54) SYSTEM AND METHOD FOR ANATOMY LABELING ON A PACS

(75) Inventors: Denny Wingchung Lau, Sunnyvale, CA (US); Yaseen Samara, Berkeley, CA (US); Vijaykalyan Yeluri, Sunnyvale, CA (US); Frank Owen, Elmhurst, IL (US); Perry Scott Frederick, Palo Alto, CA (US); Christopher Frederick Beaulieu, Los Altos, CA (US); Richard Allen Barth, Los Altos, CA (US); Garry Evan Gold, Stanford, CA (US); David Seungwon Paik, Half Moon Bay, CA (US); Raghav Raman, Cupertino, CA (US); Steven P. Roehm, Waukesha, WI (US); Robert John Herfkens, Stanford, CA (US)

(73) Assignee: General Electric Company, Schenectady, NY (US)

( * ) Notice: Subject to any disclaimer, the term of this patent is extended or adjusted under 35 U.S.C. 154(b) by 660 days.

(21) Appl. No.: 11/273,285

(22) Filed: Nov. 14, 2005

(65) Prior Publication Data
US 2007/0127790 A1 Jun. 7, 2007

(51) Int. Cl.
*A61B 5/05* (2006.01)
*G06K 9/00* (2006.01)

(52) U.S. Cl. ............................ 600/413; 382/128; 378/62

(58) Field of Classification Search ................. 382/100, 382/128, 129, 130, 131, 132, 133, 134, 154, 382/155, 156, 162, 168, 181, 189, 196, 203, 382/209, 232, 255, 274, 276, 285, 294, 305, 382/312; 378/62; 600/413, 437
See application file for complete search history.

(56) References Cited

U.S. PATENT DOCUMENTS 6,425,865 B1 * 7/2002 Salcudean et al. ........... 600/437

(Continued)

FOREIGN PATENT DOCUMENTS

WO  WO0243003 A1  5/2002

(Continued)

OTHER PUBLICATIONS

Ganser, et al. "A defrmable digital brain atlas system according to Talairach and Tournoux," Medical Image Analysis 2004 Netherlands, 8(1):3-22 (2004) XP002423541 ; ISSN: 1361-8415.*

(Continued)

*Primary Examiner*—Seyed Azarian
(74) *Attorney, Agent, or Firm*—Hanley, Flight & Zimmerman, LLC (57) ABSTRACT

Certain embodiments of the present invention provide a system and method for image registration and display of relevant information. The method includes identifying one or more anatomical parts in an acquired image, mapping the acquired image to a reference image based on the one or more anatomical parts, storing anatomy information in relation to the acquired image, and displaying the acquired image based on the anatomy information. The method may also include controlling the displaying of the acquired image based on a voice command related to the anatomy information. Anatomy information may be displayed with the acquired image. Anatomy information may include clinical information, reference information, disease process information, a related image, and/or drug interaction information, for example. The acquired image may be displayed according to a display setting, such as a window level setting and/or other display setting, based on the anatomy information.

18 Claims, 6 Drawing Sheets

U.S. PATENT DOCUMENTS

| | | | |
|---|---|---|---|
| 6,674,879 B1* | 1/2004 | Weisman et al. | 382/128 |
| 7,142,633 B2* | 11/2006 | Eberhard et al. | 378/62 |
| 7,149,333 B2* | 12/2006 | Pieper et al. | 382/128 |
| 7,158,692 B2* | 1/2007 | Chalana et al. | 382/294 |
| 7,343,030 B2* | 3/2008 | Sawyer | 382/128 |
| 7,418,120 B2* | 8/2008 | Weiner et al. | 382/128 |
| 2003/0228042 A1 | 12/2003 | Sinha | |
| 2004/0193049 A1 | 9/2004 | Greenberg | |

FOREIGN PATENT DOCUMENTS

WO    WO03045222 A1    6/2003

OTHER PUBLICATIONS

Rohlfing, et al., "Quo Vadis, Atlas-Based Segmentation?" Preprint of chapter in the Handbook fo Medical Image Analysis; 111:1-55 (Mar. 27, 2005)XP002423670; XP00242367.*

Rohlfing, et al., "Quo Vadis, Atlas-Based Segmentation?" Preprint of chapter in the Handbook fo Medical Image Analysis; III:1-55 (Mar. 27, 2005) XP002423670; XP002423670.

Brown, et al. "chapter 7: Medical Image Interpretation" Handbook of Medical Imaging,Eds. Sonka M. Fitzpatrick J M. May 2000 2:399-445; XP002441394.

Sinha et al. "A customizable MR brain imaging atlas of structure and function for decision support," AMIA 2003 Annual Symposium Proceedings, Nov. 2003 pp. 604-608, XP002440952; ISSN: 1559-4076.

Raman et al., "Automated creation of radiology teaching modules: demonstration of PACS Integration and Distribution" Proceeding of Spie, Medical Imaging 2002: Pacs and Integrated Medical Information Systems: design and evaluation 4685:373-380 (May 2002) XP002440953.

Langlotz, Enhancing the expressiveness of structured reporting systems,: Journal of Digital Imaging, Unders, Philadelphia, PA, SA, 13(2)(Suppl01):49-53 (May 2000); XP009068454; ISSN: 8-08970-1889.

* cited by examiner

FIG. 1

SYSTEM AND METHOD FOR ANATOMY LABELING ON A PACS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to anatomy labeling on a picture archiving and communication system (PACS). In particular, the present invention relates to anatomy labeling on a PACS to enable anatomy specific image presentation and analysis.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

A PACS may connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining healthcare operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

PACS are complicated to configure and to operate. Additionally, use of PACS involves training and preparation that may vary from user to user. Thus, a system and method that facilitate operation of a PACS would be highly desirable. A need exists for a system and method that improve ease of use and automation of a PACS.

Computed tomography ("CT") exams may include images that are acquired from scanning large sections of a patients' body. For example, a chest/abdomen/pelvis CT exam includes one or more images of several different anatomy. Each anatomy may be better viewed under different window level settings, however. Thus, when a radiologist or other personnel is interpreting a chest/abdomen/pelvis CT exam, he or she switches among different window level settings to view images for different anatomy, for example. It would benefit radiologists and other personnel if the window level setting(s) were automatically adjusted for them based on the image(s)/anatomy(ies) that they are viewing.

Currently, image review workstations cannot correlate image content to anatomy to facilitate presentation of relevant anatomical data. However, healthcare personnel, such as radiologists, may be interested to view information about specific anatomical structures and/or other patient data when viewing and/or interpreting patient image(s). For example, when a radiologist is viewing a CT axial image that contains the liver, he or she may want to learn about the disease processes associated with the liver or the patient's lab tests associated with the liver. Thus, an image review workstation having the capability to recognize an anatomy of interest, such as a liver, and search for and present anatomy-related information to a user would be highly desirable.

During an exam interpretation process, radiologists and/or other healthcare personnel may like to note image findings as a mechanism to compose reports. In the case of structured reports, radiologists have found that the mechanism to input data is too cumbersome. That is, since there are so many possible findings related to an exam procedure, the findings need to be categorized in some hierarchy structure. The numerous hierarchical levels and choices of selection require extensive manual manipulation from the radiologist.

For example, a chest/abdomen/pelvis CT exam may include images of the liver, pancreas, stomach, etc. If a radiologist wants to input a finding related to the liver, he or she must currently traverse through a hierarchy of choices presented in the GUI before being able to identify the desired finding.

When radiologists are viewing patients' images in the exam interpretation process, sometimes they would like to view the images specific to certain organs. For example, a patient with a history of colon cancer has a CT exam that contains images of the stomach, small intestine, liver, pancreas, colon, etc. A radiologist may want to first view the images of the colon. If the colon does not demonstrate any remarkable abnormalities, then the radiologist may suspect that the reported symptoms are related to ailments in the liver and wants to view the images containing the liver. However, there is currently no method on image review workstations that enables a radiologist to view images specific to organs. A radiologist can only view images in sequential order.

Thus, there is a need for a system and method for improved image presentation and analysis. There is a need for a system and method for anatomy labeling to facilitate anatomy specific image presentation and analysis.

BRIEF SUMMARY OF THE INVENTION

Certain embodiments of the present invention provide a system and method for image registration and display of relevant information. Certain embodiments provide an image registration system for correlating clinical information with at least one image. The system includes a reference image set including one or more reference images and an image registration module for registering one or more acquired images with the reference image set. At least one reference anatomy is identified in each of the one or more reference images. Relevant anatomy information is correlated with at least one reference anatomy in each of the one or more reference images. The image registration module registers at least one acquired anatomy in the one or more acquired images with the reference image set. The image registration module associates the relevant anatomy information with the one or more acquired images based on the reference image set.

In an embodiment, the system may include more than one reference image set based on patient characteristics. Patients characteristics include weight, height, gender, ethnicity, etc. Combinations of patient characteristics may represent different reference sets, for example. In an embodiment, a newly acquired image exam may be categorized based on different characteristics associated with a reference image set.

In an embodiment, the system further includes a display module capable of displaying one or more acquired images and the associated relevant anatomy information. The relevant information may be stored as meta-data associated with one or more acquired images, for example. In an embodiment, the relevant anatomy information comprises clinical information relevant to the at least one acquired anatomy. In an embodiment, the relevant anatomy information includes a window level setting for display of one or more acquired images based on anatomy.

In an embodiment, the relevant anatomy information allows a user to request an image based on a voice command. The voice command may relate to an anatomy in the one or more acquired images, for example. In an embodiment, the relevant anatomy information is capable of narrowing a structured report finding selection based on at least one anatomy.

Certain embodiments provide a computer-readable storage medium including a set of instructions for execution on a processor, such as a computer or other processing device. The set of instructions includes an image registration routine configured to register acquired images with respect to at least one reference set of images, wherein the at least one reference set of images is associated with relevant anatomical information, and a display routine for displaying the acquired images based on the relevant anatomical information. In an embodiment, the relevant anatomical information facilitates voice navigation of the acquired images based on anatomy. In embodiment, the relevant anatomical information includes patient clinical information, reference sources, diseases processes, related images, and/or drug interactions, for example.

In an embodiment, the relevant anatomical information is displayed with the acquired images. In an embodiment, the relevant anatomical information specifies a display setting, such as a window level setting, for display of at least one of the acquired images. The relevant anatomical information may include a plurality of display settings with associated priorities, wherein the acquired images are displayed according to an anatomy having a highest associated priority in the acquired images. In an embodiment, the relevant anatomical information is capable of narrowing selection of finding for entry into a structured report.

Certain embodiments provide a method for correlating anatomy in an acquired image with a reference image. The method includes identifying one or more anatomical parts in an acquired image, mapping the acquired image to a reference image based on the one or more anatomical parts, storing relevant anatomy information in relation to the acquired image, and displaying the acquired image based on the relevant anatomy information. The method may also include controlling the displaying of the acquired image based on a voice command, wherein the voice command is related to the relevant anatomy information.

In an embodiment, the relevant anatomy information is displayed with the acquired image. The relevant anatomy information may include clinical information, reference information, disease process information, a related image, and/or drug interaction information, for example. In an embodiment, a list of findings may be displayed for entry in a structured report, wherein the list of findings is tailored to the relevant anatomy information. In an embodiment, the acquired image is displayed according to a display setting, such as a window level setting and/or other display setting, based on the relevant anatomy information.

Certain embodiments provide a method for constructing a structured report based on image anatomy. The method includes identifying anatomical structures in an image, mapping the anatomical structures to a reference image set, and presenting a list of image findings associated with the anatomical structures for entry into a structured report.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
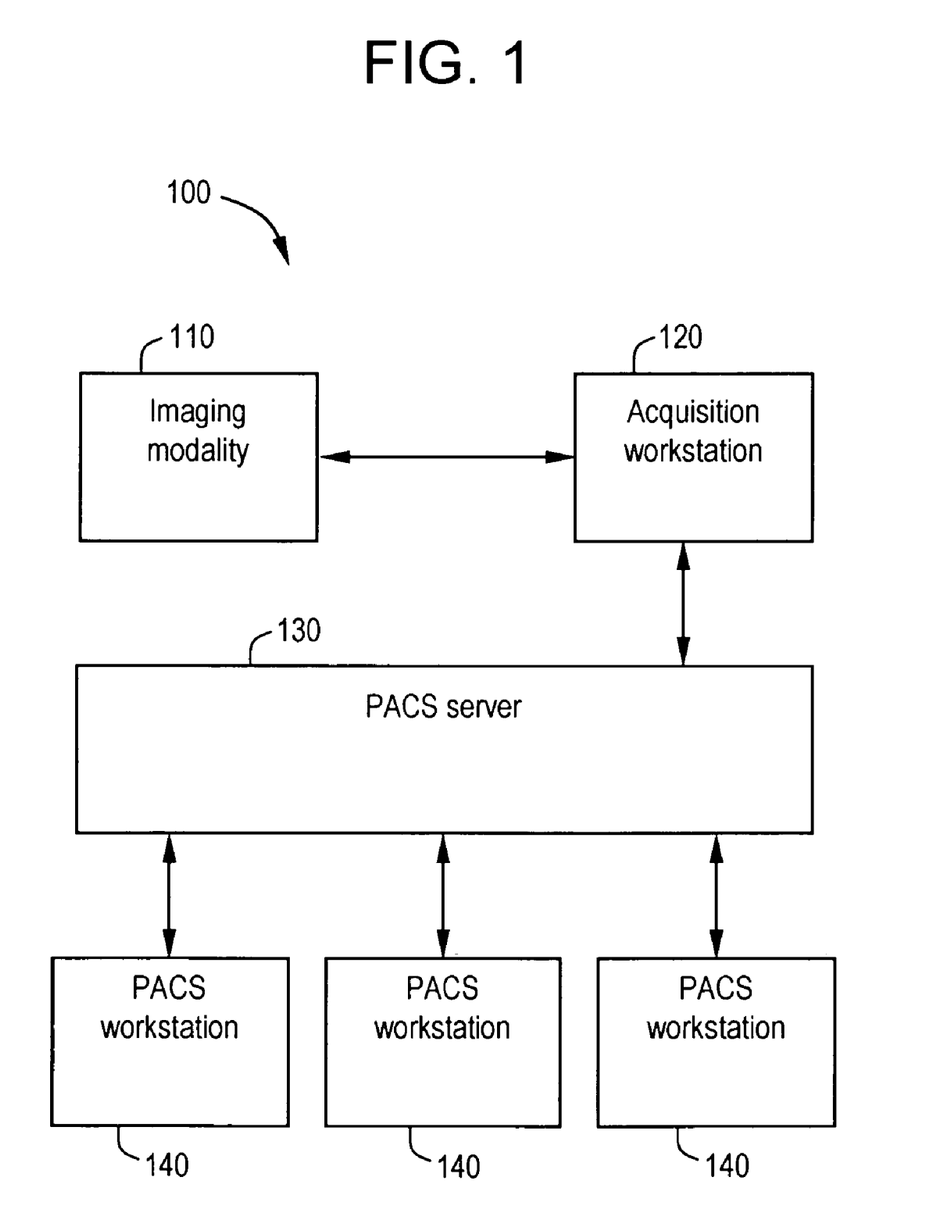
FIG. 1 illustrates an exemplary picture archiving and communication system used in accordance with an embodiment of the present invention.

FIG. 1 illustrates an exemplary Picture Archiving and Communication System (PACS) 100 used in accordance with an embodiment of the present invention. The PACS system 100 includes an imaging modality 110, an acquisition workstation 120, a PACS server 130, and one or more PACS workstations 140. The system 100 may include any number of imaging modalities 110, acquisition workstations 120, PACS server 130 and PACS workstations 140 and is not in any way limited to the embodiment of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography ("CR") image of a patient's chest. A radiologist or user may then examine the image for any objects of interest, such as tumors, lesions, etc., for example.

The PACS workstations 140 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In an embodiment, the PACS system 100 includes a perspectives manager capable of being used for reviewing images via a plurality of perspectives. The PACS server 130 and/or a PACS workstation 140 may include the perspectives manager, or the perspectives manager may be implemented in a separate system. In an embodiment, each PACS workstation 140 may include a perspectives manager.

A user may wish to apply additional processing steps to one or more images to further enhance features in the image. For example, a user may desire to apply additional processing functions or steps to an image in order to alter the presentation of an image in conformance with the user's confidence level for making an accurate diagnosis. In other words, different users may desire to apply different or additional processing steps than are included in a default image processing workflow.

The additional image processing step(s) may include any image processing step useful to prepare an image for a diagnostic examination. For example, as described above, an image processing step (as a default image processing step or an additional image processing step) can include flipping an image, zooming in an image, panning across an image, and altering one or more of a window, a level, a brightness and a contrast setting of an image.

PACS workstations 140 may retrieve or receive image data from server 130 for display to one or more users. For example, a PACS workstation 140 may retrieve or receive image data representative of a computed radiography image of a patient's chest. A radiologist may then examine the image as displayed on a display device for any objects of interest such as, for example, tumors, lesions, etc.

PACS workstations 140 are also capable of or configured to retrieve and/or receive one or more hanging protocols from server 130. For example, a default hanging protocol may be communicated to PACS workstation 140 from server 130. A hanging protocol may be communicated between server 130 and a PACS workstation 140 over a wired or wireless connection, for example.

In general, PACS workstations 140 may present images representative of image data retrieved and/or received from server 130. PACS workstations 140 may present the images according to a hanging protocol. As described above, a hanging protocol is a set of display rules for presenting, formatting and otherwise organizing images on a display device of a PACS workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a PACS workstation 140 to display an anterior-posterior ("AP") image adjacent to a lateral image of the same anatomy. In another example, a hanging protocol may direct PACS workstation 140 to display the AP image before displaying the lateral image. In general, a hanging protocol dictates the spatial and/or temporal presentation of a plurality of images at PACS workstation 140.

A hanging protocol differs from a default display protocol ("DDP"). In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or functions that are applied before any diagnostic examination of the images. For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users.

Conversely, applying a hanging protocol to image data does not alter the appearance of an image (based on the image data), but instead dictates how the image(s) is(are) presented, as described above.

Server 130 may store a plurality of hanging protocols and/or DDPs. The hanging protocols and/or DDPs that are stored at server 130 and have not yet been modified or customized are default hanging protocols/DDPs. A default hanging protocol and/or DDP may be selected from a plurality of default hanging protocols and/or DDPs based on any number of relevant factors such as, for example, a manual selection, a user identity, and/or pre-processing of the image data.

Specifically, a default hanging protocol and/or DDP may be selected based on a manual selection simply by communicating the default protocol once a user has selected that particular protocol. The user may make the selection, for example, at a PACS workstation 140.

In another example, a default protocol may be selected based on a user identity. For example, a user may have a preferred DDP. The DDP may have been customized to meet the user's preferences for a particular temporal and/or spatial layout of images. Once a user gains access to a PACS workstation 140 (for example, by entering a correct login and password combination or some other type of user identification procedure), the preferred DDP may be communicated to the PACS workstation 140, for example.

In another example, a default protocol may be selected based on pre-processing of image data. Pre-processing of image data may include any image processing known to those of ordinary skill in the art that prepares an image for review by a user. Pre-processing may also include, for example, a computer-aided diagnosis ("CAD") of image data. CAD of image data may include a computer (or similar operating unit) automatically analyzing image data for objects of interest. For example, a CAD may include a software application that analyzes image data for nodules in images of lungs, lesions, tumors, etc. However, a CAD application can include any automatic analysis of image data known to those of ordinary skill in the art.

For example, a default hanging protocol that corresponds to CAD findings of lung tumors may provide for the presentation of the posterior-anterior ("PA") and lateral lung images adjacent to each other followed by the presentation of the computer tomography ("CT") lung images, followed by the magnetic resonance ("MR") lung images, for example. In general, a default hanging protocol that corresponds to CAD findings is designed to present images in a spatial and/or temporal layout that is useful to a radiologist. For example, a radiologist may be greatly assisted in his or her review of the CAD findings by viewing the PA and lateral lung images adjacent to each other, followed by previously acquired multi-slice CT and MR images of the lungs.

Therefore, based on CAD findings, a default protocol may be selected from a plurality of default protocols and applied at a workstation 140 in order to present images to a user.

In an embodiment, a reference set of images may be collected and stored at a PACS (e.g., PACS server 130 and/or workstation 140) or other image data storage, for example. Reference images may be an aggregated set of references or "gold standard" images and/or may be organized for a particular patient, for example. For example, five sets of images may serve as a reference set for acquired image data. Images in the reference set(s) are labeled with major anatomy or other feature(s) in each image. Once image registration has been performed, acquired image studies, such as newly acquired radiology image studies, may automatically be labeled based on the labels found in the reference image set(s). Labels may be correlated for newly acquired images at a patient level, organ level, etc. For example, a liver may be identified in a newly acquired image based on registration between the newly acquired image and one of the reference images. A label assigned to a structure, such as a liver, in the reference image(s) is assigned to the corresponding structure in the acquired image.

In an embodiment, a user may navigate through a plurality of images based on labels assigned to one or more features in the images. In an embodiment, voice command may be used to navigate a plurality of images in a study based on labels. For example, a radiologist may say "liver", and a PACS automatically displays a first liver image in a study. Thus, a user may navigate set of images by anatomy, such as by organ. Alternatively, a user may navigate a set of images by patient, such as by saying a patient name or identifier, or by other criterion.

In an embodiment, a library of standard or typical scans may be classified by one or more characteristic, such as modality, patient, gender, weight, height, age, ethnicity, ailment, etc. Any number of images may be included and classified in the library. A reference set of images may be selected from the library based on one or more characteristics. A PACS may automatically match a reference set to the desired characteristic(s) based on data input at time of image acquisition, for example. In an embodiment, the system may include more than one reference image set based on patient characteristics. Combinations of patient characteristics may represent different reference sets, for example. In an embodiment, a newly acquired image exam may be categorized based on different characteristics associated with a reference image set.

In an embodiment, clinical information may be displayed based on anatomy. For example, a patient may have pathology, lab results, microbiology, historical data, etc. as well as images. When a radiology or other healthcare practitioner is examining images, he or she may wish to also consider clinical information, such as test results, etc. Additionally, results may only be relevant to certain parts of anatomy. If a PACS determines which images and/or anatomy a practitioner is reviewing, the PACS may automatically display relevant results. A PACS or other system may map results and/or other data with relevant anatomy. The PACS registers viewed image(s) to reference image(s). Based on registration, the PACS may determine anatomy and retrieve relevant data mapped to the anatomy.

Figure 2:
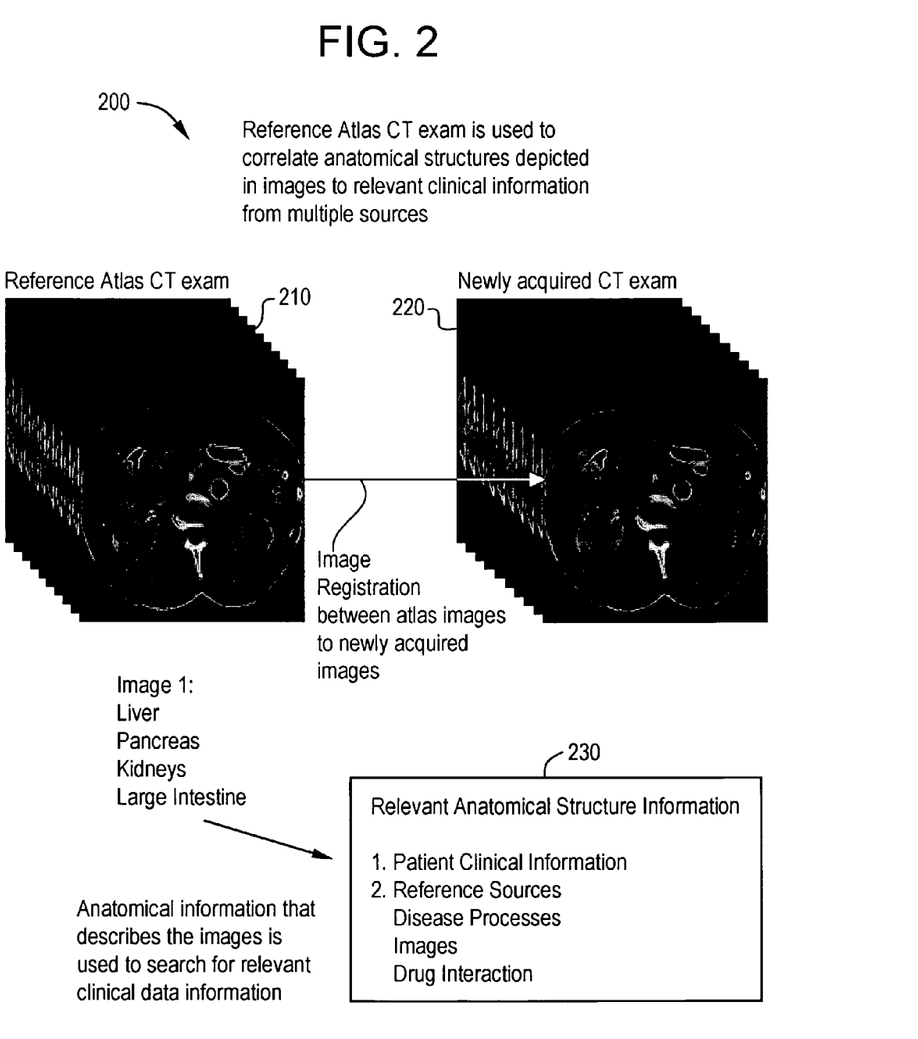
FIG. 2 illustrates an image registration system for registering images with respect to a reference image set in accordance with an embodiment of the present invention.

FIG. 2 illustrates an image registration system 200 for registering images with respect to a reference image set in accordance with an embodiment of the present invention. The system 200 includes a reference image set 210, an acquired image set 220, and anatomical structure or clinical information 230. The reference image set 210 and acquired image set 220 may include images of the same or related modality, for example. Alternatively, the reference image set 210 and acquired image set 220 may include images of different modalities. The reference image set 210 and/or acquired image set 220 may include one or more images obtained from CT, MR, digital radiography ("DR"), x-ray, ultrasound, nuclear, single phone emission computed tomography ("SPECT"), positron emission tomography ("PET"), and/or other imaging systems. For example, the reference image set 210 may include one or more images depicting a plurality of anatomy, such as liver, pancreas, kidneys, and/or large intestine, in an image. The reference image set 210 and/or acquired image set 220 may include one or more subsets of images. In an embodiment, the reference image set 210 and/or a subset of the reference image set 210 may be organized by anatomy, malady, patient, and/or other criterion. The acquired image set 220 and/or a subset of the acquired image set 220 may also be organized by anatomy, malady, patient, and/or other criterion, for example. The anatomical structure information 230 may include patient clinical information, reference sources, disease processes, images, drug interactions, and/or other information, for example.

The reference image set 210 may be used to correlate anatomical structures depicted in image(s) to relevant clinical information from one or more sources. Image registration techniques, such as cross correlation, minimization of variance, mutual information, principal axes, manual registration, and/or other registration technique, may be used to correlate image(s) and/or points within the image(s) in the acquired image set 220 with images and/or points in the reference image set 210. Anatomical information contained in the reference image set 210 describes image content in the reference image set 210. An image registration module may be used to register the acquired image set 220 with respect to the reference image set 210. The image registration module may be implemented on a PACS workstation, PACS server, image viewer, and/or other processor, for example. Image registration, display, and/or other functionality may be implemented in hardware, firmware, and/or as a set of instructions in software, for example.

Once the acquired image set 220 has been registered, the reference image set 210 may be used to retrieve relevant clinical data or other information 230. Relevant anatomical or clinical data 230 may include patient clinical information, reference sources, disease or other malady processes, related image(s), drug interaction information, and/or other information, for example.

For example, a series chest CT image of a patient may be acquired as acquired image data 220. The images include a liver, pancreas, kidneys, and large intestine of the patient, for example. The anatomy of the images is registered based on corresponding anatomy in the reference image set 210. For example, the liver in the acquired image set 220 is correlated to the liver in the reference image set 210, etc. Once the acquired images 220 are registered with respect to the reference images 210, clinical data 230 associated with the reference images 210 may be retrieved for the acquired images 220. Relevant clinical data 230 may be provided to a user along with the acquired images 220.

Figure 3:
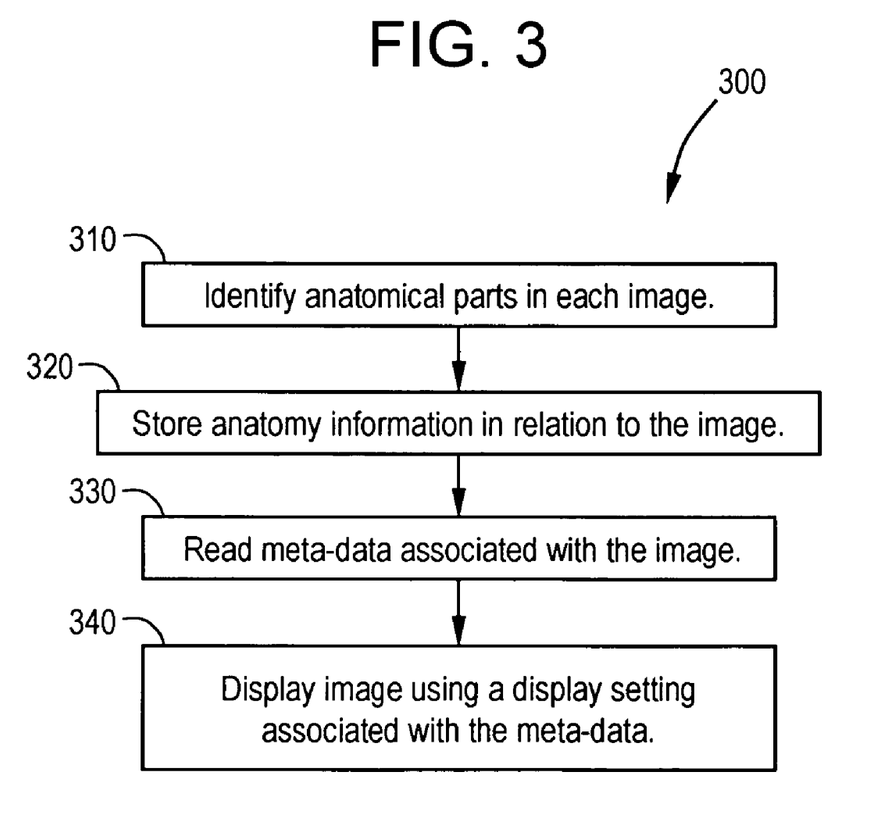
FIG. 3 illustrates a flow diagram for a method for automatic display adjustment based on image anatomy used in accordance with an embodiment of the present invention.

FIG. 3 illustrates a flow diagram for a method 300 for automatic display adjustment based on image anatomy used in accordance with an embodiment of the present invention. In an embodiment, the method 300 may be used to automatically adjust window level settings and/or other display settings for a display, such as a PACS workstation 140 display, image viewer display, and/or other display. In an embodiment, a displayed image is correlated with an anatomical body part, and the anatomical body part is then correlated with a preset window level setting, for example.

First, at step 310, major organs and/or other anatomical parts of interest are identified for each image in an exam. For example, heart, lungs, liver, kidneys, etc. may be identified in a series of images obtained for a patient. Then, at step 320, information regarding the identified anatomies in an image is stored in relation to the image. For example, information identifying the heart and lungs in an image may be stored as meta-date for that image. The meta-data may be stored as header information for the image and/or may be stored in a database that references the image, for example.

Next, at step 330, the meta-data associated with the image is read. The meta-data may be read from the image header and/or a database or other storage storing the meta-data. At step 340, a window level setting associated with the meta-data (i.e., with the anatomical parts in the image) is used to display the image. An image may be displayed on a monitor or other display associated with a PACS, an image viewer, and/or other storage system, for example.

Identification of organs and anatomical parts in images may be accomplished by a variety of methods. For example, a technologist may view each image and identify an anatomy in each image. The information may be entered into a database or other data store, for example. Alternatively, automatic image registration may be performed with a "gold" standard reference set of images. For example, a "gold" standard reference set of images may be stored in a PACS, image viewer, and/or other image storage system for each exam procedure. (e.g., a reference image set for a CT chest/abdomen/pelvis exam). Each image in the reference set is labeled with the associated prominent anatomical structures by a radiologist or other personnel manually and/or automatically. Once the anatomical labeling is performed, the reference set of images becomes an anatomical atlas. In the atlas, every image contains meta-image data that describes the associated anatomical structures. Thus, the atlas effectively has the mapping information for mapping image content to anatomical structures.

For each new exam that is acquired, the exam image(s) are registered with the relevant reference set of atlas image(s) to best match the image(s) in the newly acquired exam to image (s) in the atlas reference exam. After registration, the images in the newly acquired exam are also mapped to the anatomical structures found in the atlas reference exam. The mapping information may be indexed in a database and/or other data storage, for example. When a radiologist or other healthcare personnel is viewing an image, a system, such as a PACS or other image viewing/storage system, may automatically detect that the image contains anatomical structures A, B, C and recognizes that window level setting D should be used to display the image.

For example, a table or other data structure may be used to map an anatomy to a display window level setting and/or other display setting. Additionally, the table may include a priority for an anatomy relative to other anatomy. In an embodiment, if an image includes anatomy A, B, C and each anatomy maps to a different window level or other setting, then a prioritization scheme may be used to determine which anatomy's setting should be applied based on the anatomy's priority.

As shown in Table 1 below, if an image includes both a lung and a heart, then the window level setting is set at the window level setting for the lung since the lung has a higher priority than the heart.

TABLE 1

| Anatomy | Window Level Setting | Priority |
| --- | --- | --- |
| Lung | 1280, 400 | 1 |
| Heart | 600, 600 | 2 |
| Pancreas | 600, 400 | 3 |

Figure 4:
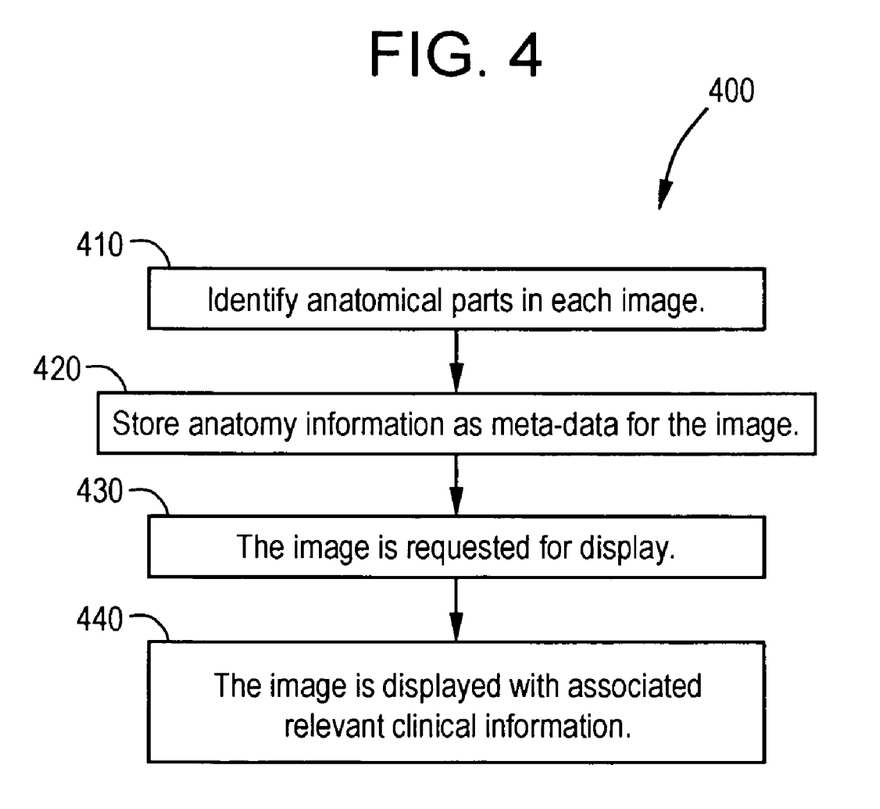
FIG. 4 illustrates a flow diagram for a method for display of images and relevant clinical information based on image anatomy used in accordance with an embodiment of the present invention.

FIG. 4 illustrates a flow diagram for a method 400 for display of images and relevant clinical information based on image anatomy used in accordance with an embodiment of the present invention. At step 410, for each image, major organ(s) and/or other anatomical part(s) of interest are identified. Items of interest in an image may be identified manually and/or automatically, as described above in relation to FIG. 3.

Then, at step 420, information related to items of interest in an image is stored as meta-data for that image. The meta-data may be stored as header information and/or in a database or other data structure that associates the image and the meta-data. At step 430, the image is requested for display. For example, the image is retrieved for display at a PACS workstation or image viewer. At step 440, when the image is displayed, the meta-data is read, and the relevant clinical information associated with the anatomical parts is also displayed.

Identification of organs and anatomical parts in the images may be accomplished by a variety of methods, including manual and automatic analysis as described above. A reference set of images is stored in a PACS and/or other image viewing or analysis system for each exam procedure, for example. Each image in the reference set is labeled with associated prominent anatomical structures. Once the anatomical labeling is performed, the reference set of images becomes an anatomical atlas. In the anatomical atlas, every image contains meta-image data that describes the associated anatomical structures. Thus, the anatomical atlas effectively has mapping information for mapping image content to anatomical structures.

For each new exam that is acquired, the exam is registered with the relevant reference set of atlas images to best match the images in the newly acquired exam to the atlas reference exam. After the registration, the images in the newly acquired exam are also mapped to the anatomical structures in the atlas. The anatomical mapping information may be indexed in a database or other data structure. When a user views the images, the viewing system, such as a PACS workstation or image viewer, recognizes that the image is associated with anatomical structures A, B, C and presents clinical information, such as disease process and patient information, associated with anatomical structures A, B, C to the user.

Figure 5:
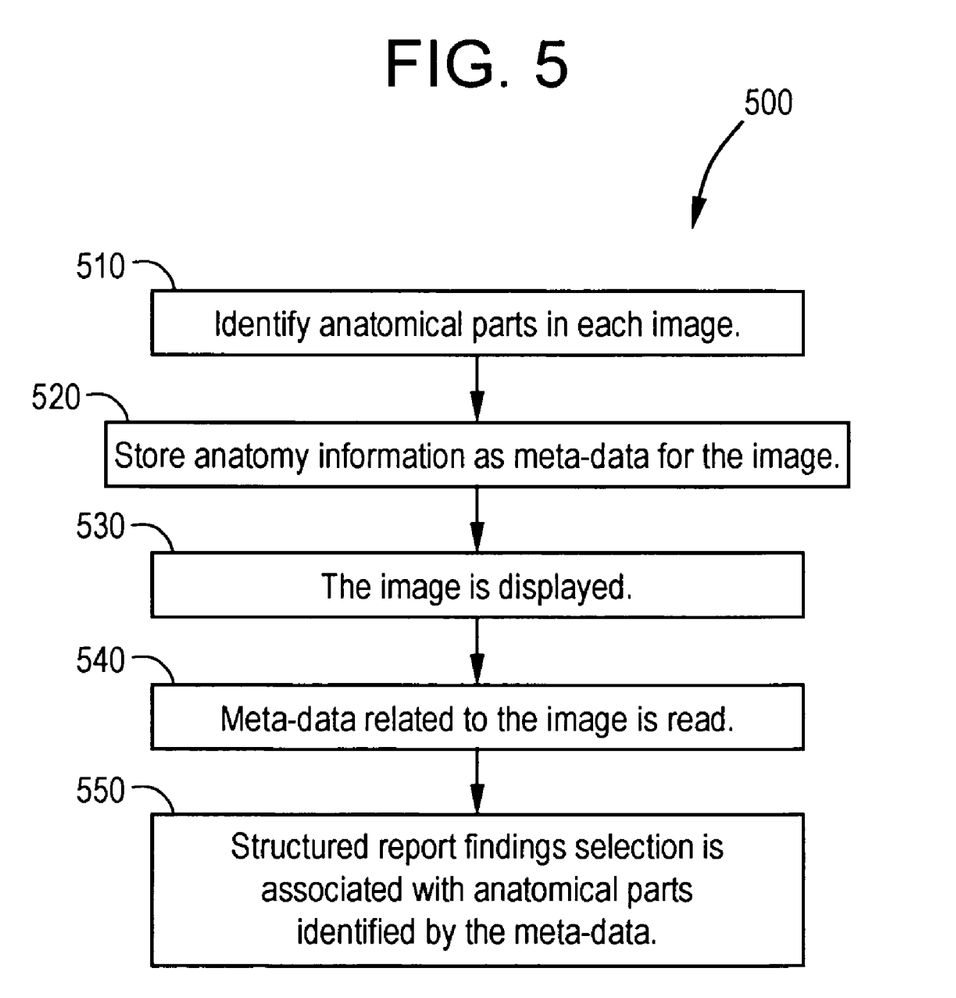
FIG. 5 depicts a flow diagram for a method for simplifying image reporting in accordance with an embodiment of the present invention.

FIG. 5 depicts a flow diagram for a method 500 for simplifying image reporting in accordance with an embodiment of the present invention. In an embodiment, image reporting hierarchy may be simplified by presenting only findings that are related to anatomy contained in an image. Thus, instead of presenting choices that are relevant to all images in an exam, only the choices relevant to the displayed image are presented. To display choices specific to an image, content in one image is differentiated from another image in the exam. For example, image content may be differentiated based on body organs contained in the images.

At step 510, organs and/or other anatomical parts of interest may be identified in each acquired image. Then, at step 520, the identified anatomical information is stored as meta-data for the image (e.g., as header information or in a database). Next, at step 530, the image is displayed. At step 540, the related image meta-data is read. Then, at step 550, structured report findings selection is associated with the anatomical parts identified by the meta-data.

Identification of organs and/or other anatomical parts in image(s) may be accomplished by a variety of methods. For example, a technologist may manually view each image, identify anatomy in each image, and enter that information into a database or other data structure. An automatic method may be to perform automatic image registration with a gold standard reference set of images. A gold standard reference set of images may be stored for each exam procedure, for example. Each image in the reference set may be labeled with associated prominent anatomical structures (e.g., automatically by a PACS and/or manually by a radiologist or other personnel). Once anatomical labeling is performed, the reference set of images becomes an anatomical atlas. In the atlas, every image contains meta-image data that describes the associated anatomical structures. Thus, the atlas effectively has the mapping information for mapping image content to anatomical structures.

For each new exam that is acquired, the exam image(s) are registered with a relevant reference set of atlas images to best match the images in the newly acquired exam to the atlas reference exam. After registration, the images in the newly acquired exam are also mapped to anatomical structures in the reference exam. Mapping information may be indexed in a database or other data structure, for example. A radiologist or other user viewing an image may want to input a finding into a structured report. Anatomical structures, such as anatomical structures A, B, C, associated with the image may be identified based on mapping information. Then, a list of findings associated only with anatomical structures A, B, C may be presented to the viewer, such as a radiologist or other healthcare personnel.

Figure 6:
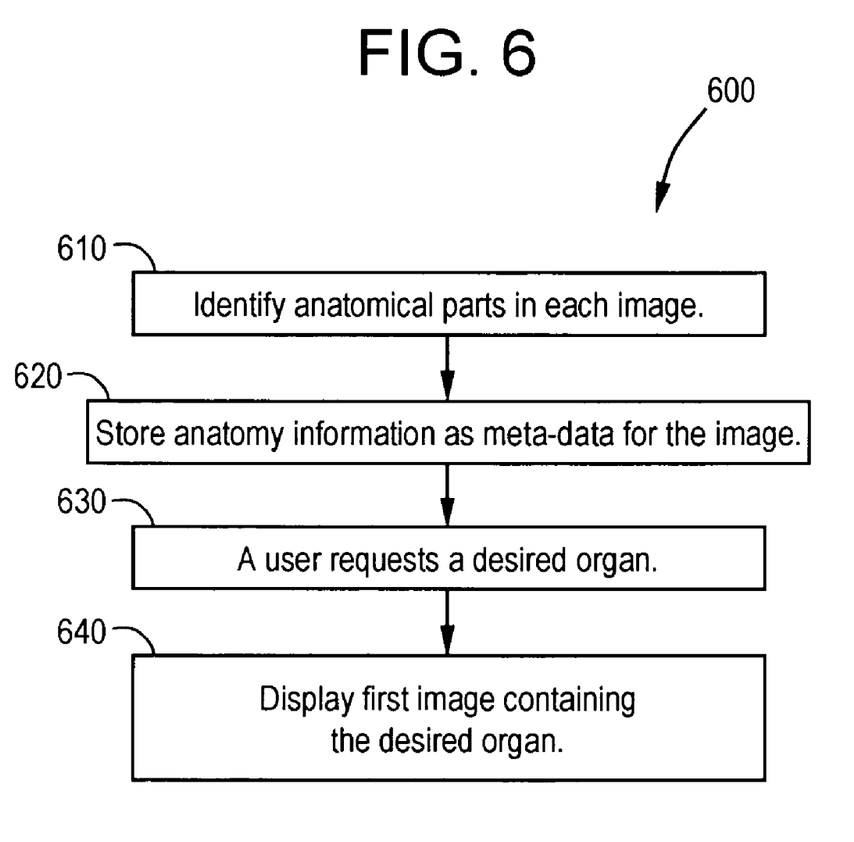
FIG. 6 depicts a flow diagram for a method for identifying items in an image in accordance with an embodiment of the present invention.

FIG. 6 depicts a flow diagram for a method 600 for identifying items in an image in accordance with an embodiment of the present invention. To enable display of image(s) specific to organs, content in each image may be identified. First, at step 610, organs and/or other anatomical parts of interest may be identified for each image. Identification of items, such as organs and/or anatomical parts in image(s), may be accomplished by a variety of methods, such as manual entry of anatomy information into a database or other data structure and/or automatic image registration with a reference set of images. Each image in a reference set may be labeled with associated anatomical structures. Once anatomical labeling is performed, the reference set of images becomes an anatomical atlas. Each image in the anatomical atlas includes meta-image data that describes the associated anatomical structures. The atlas includes information mapping image content to anatomical structures.

Newly acquired images are registered with a reference set of atlas images to match the images in the newly acquired exam to the atlas reference exam. After registration, the images in the newly acquired exam are also mapped to the anatomical structures.

At step 620, anatomical identification information is stored as meta-data for that image. The meta-data may be stored in a plurality of way, such as storing meta-data as header information for the image or in a database, table, or other data structure in reference to the image. The mapping information may be indexed in the database or other data structure, for example.

At step 630, a user may request a desired organ. For example, a user may input a desired organ name into software on a PACS workstation, image viewer, and/or other system. Alternatively, a user may speak the name of a desired organ, and a voice recognition engine translates the voice data to text data to identify relevant image data. At step 640, based on the name of the desired organ, a first image in a sequence containing the desired organ is displayed. Thus, for example, a radiologist may verbally request liver images for a patient, and the first image in a series of liver images for the patient is retrieved and displayed on a PACS display, for example. Subsequent liver images may similarly be displayed. A user may also retrieve related clinical information related to the patient and/or anatomy in the images, for example. A user may also switch to a different patient and/or anatomy based on input and/or voice commands, for example.

Certain embodiments may be provided as a set of instructions residing on a computer-readable medium, such as a memory or hard disk, for execution on a computer or other processing device, such as a PACS workstation or image viewer.

Thus, certain embodiments provide automatic application of display settings, such as window level setting presets, based on anatomy in image(s) being displayed. Certain embodiments provide a capability to navigate through a plurality of images by anatomy in addition to serial navigation. Thus, a user, such as a radiologist, does not need to manually search for images containing a desired anatomy to view. Certain embodiments allow a user to navigate images based on voice commands as well as keyboard or mouse input. Additionally, certain embodiments improve usability of structured reporting by dynamically filtering choices to input findings and other information in a structured report. Certain embodiments correlate image content to textual and other data to enable presentation of image-specific findings selection for input to a structured report.

Certain embodiments reduce time used by radiologists and other healthcare personnel to search for related anatomical information. Certain embodiments display image(s) as well as anatomical information related to displayed image(s) for review by a user. Certain embodiments correlate image content to textual and other data to enable searching and presentation of relevant anatomical information from reference sources and patient's clinical history. Certain embodiments allow users, such as radiologists and other healthcare personnel to make a more accurate diagnosis when armed with more relevant clinical and reference information, for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An image registration system for correlating clinical information with at least one image, said system comprising:
a reference image set comprising one or reference images, wherein at least one reference anatomy is identified in each of said one or more reference images, and relevant anatomy information is correlated with said at least one reference anatomy in each of said one or more reference images;
an image registration module registering one or more acquired images with said reference image set, wherein said image registration module registers at least one acquired anatomy in said one or more acquired images with said reference image set, and wherein said image registration module associates said relevant anatomy information with said one or more acquired images based on said reference image set; and
a display module displaying said one or more acquired images and said associated relevant anatomy information, wherein said display module automatically adjusts display settings for said one or more acquired images based at least in part on said anatomy information,
wherein said relevant anatomy information includes a plurality of display settings with associated priorities, and wherein said acquired images are displayed according to an anatomy having a highest associated priority in said acquired images, and wherein said relevant anatomy information is capable of narrowing selection of a finding for entry into a structured report.

2. The system of claim 1, wherein said relevant anatomy information comprises clinical information relevant to said at least one acquired anatomy.

3. The system of claim 1, wherein said relevant anatomy information is stored as meta-data associated with said one or more acquired images.

4. The system of claim 1, wherein said relevant anatomy information includes a window level setting for display of said one or more acquired images based on anatomy.

5. The system of claim 1, wherein said relevant anatomy information allows a user to request an image based on a voice command.

6. The system of claim 5, wherein said voice command relates to an anatomy in said one or more acquired images.

7. A computer-readable storage medium including a set of instructions for execution on a processor, the set of instructions comprising:
an image registration routine configured to register acquired images with respect to at least one reference set of images, wherein said at least one reference set of images is associated with relevant anatomical information, and wherein at least one reference anatomy is identified in each image of said at least one reference set of images and said relevant anatomical information is correlated with said at least one reference anatomy in each image of said at least one reference set of images, wherein said image registration routine associates said relevant anatomical information with said acquired images based on said at least one reference set of images; and a display routine for displaying said acquired images based on said relevant anatomical information, wherein said display routine automatically adjusts display settings for said acquired images based at least in part on said relevant anatomy information, wherein said relevant anatomical information includes a plurality of display settings with associated priorities, and wherein said acquired images are displayed according an anatomy having a highest associated priority in said acquired images, and wherein said relevant anatomical information is capable of narrowing selection of finding for entry into a structured report.

8. The computer-readable storage medium of claim 7, wherein said relevant anatomical information facilitates voice navigation of said acquired images based on anatomy.

9. The computer-readable storage medium of claim 7, wherein said relevant anatomical information comprises at least one of patient clinical information, reference sources, diseases processes, related images, and drug interactions.

10. The computer-readable storage medium of claim 7, wherein said relevant anatomical information is displayed with said acquired images.

11. The computer-readable storage medium of claim 7, wherein said display setting comprises a window level setting for display of at least one of said acquired images.

12. A computer-implemented method for correlating anatomy in an acquired image with a reference image, said method comprising:

identifying, using a computer, one or more anatomical parts in an acquired image;

mapping said acquired image to a reference image based on said one or more anatomical parts;

storing relevant anatomy information in relation to said acquired image, wherein at least one reference anatomy is identified in said reference image, and said relevant anatomy information is correlated with said at least one reference anatomy in said reference image, and wherein said relevant anatomy information is associated with said acquired image based on said reference image; and displaying said acquired image based on said relevant anatomy information, wherein displaying automatically adjusts display settings for said acquired image based at least in part on said relevant anatomy information, wherein said relevant anatomy information includes a plurality of display settings with associated priorities, and wherein said acquired image is displayed according to an anatomy having a highest associated priority in said acquired image, and wherein said relevant anatomy information is capable of narrowing selection of a finding for entry into a structured report.

13. The method of claim 12, further comprising controlling said displaying of said acquired image based on a voice command, wherein said voice command is related to said relevant anatomy information.

14. The method of claim 12, wherein said displaying step further comprises displaying said relevant anatomy information with said acquired image, wherein said relevant anatomy information comprises at least one of clinical information, reference information, disease process information, a related image, and drug interaction information.

15. The method of claim 12, wherein said displaying step further comprises displaying a list of findings for entry in a structured report, wherein said list of findings is tailored to said relevant anatomy information.

16. The method of claim 12, wherein said display setting comprises a window level setting.

17. The method of claim 12, wherein said acquired image is mapped to said reference image based on at least one patient characteristic.

18. A computer-implemented method for constructing a structured report based on image anatomy, said method comprising:

identifying, using a computer, anatomical structures in an acquired image;

registering said acquired image with said reference image set and mapping said anatomical structures in said acquired image to a reference image set comprising one or more reference images, wherein at least one reference anatomy is identified in said reference image and relevant anatomy information is correlated with said at least one reference anatomy in said reference image, wherein said relevant anatomy information is associated with said acquired image based on said reference image;

providing automatic adjustments for image display settings based on said anatomical structures and image findings related to said anatomical structures wherein a plurality of image display settings include associated priorities and wherein said image is displayed according to an anatomy having a highest associated priority; and presenting a list of image findings associated with said anatomical structures for entry into a structured report, wherein said anatomical structures and image finding are capable of narrowing selection of a finding for entry into a structured report.

* * * * *

UNITED STATES PATENT AND TRADEMARK OFFICE
CERTIFICATE OF CORRECTION

PATENT NO. : 7,590,440 B2 Page 1 of 1
APPLICATION NO. : 11/273285
DATED : September 15, 2009
INVENTOR(S) : Lau et al.

It is certified that error appears in the above-identified patent and that said Letters Patent is hereby corrected as shown below:

Column 14, line 12 (Claim 1): should read "a reference image set comprising one or more reference images,"

Column 15, lines 8/9 (Claim 7): should read "...according to an anatomy having a highest associated priority in"

Column 15, lines 11/12 (Claim 7): should read "...selection of a finding for entry into a structured report."

Column 16, line 38 (Claim 18): should read "findings related to said anatomical structures, wherein a"

Column 16, line 44 (Claim 18): should read "wherein said anatomical structures and image findings"

Column 16, line 46 (Claim 18): should read "into --a-- said structured report."

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO.      : 7,590,440 B2                                Page 1 of 1
APPLICATION NO. : 11/273285
DATED           : September 15, 2009
INVENTOR(S)     : Lau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 965 days.

Signed and Sealed this

Twenty-first Day of September, 2010

David J. Kappos
*Director of the United States Patent and Trademark Office*